United States Patent [19]
Horie et al.

[11] Patent Number: 5,281,204
[45] Date of Patent: Jan. 25, 1994

[54] DEVICE FOR FORMING AN INSERTING HOLE AND METHOD OF USING AND MAKING THE SAME

[75] Inventors: Masao Horie, Otsu; Shoji Kawamoto, Takatsuki, both of Japan

[73] Assignee: NISSHO Corporation, Osaka, Japan

[21] Appl. No.: 68,262

[22] Filed: May 28, 1993

Related U.S. Application Data

[63] Continuation of Ser. No. 895,419, Jun. 5, 1992, abandoned, which is a continuation of Ser. No. 630,582, Dec. 20, 1990, abandoned.

[30] Foreign Application Priority Data

Dec. 26, 1989 [JP] Japan .................. 1-337658

[51] Int. Cl.$^5$ .................................... A61B 17/34
[52] U.S. Cl. .................................... 604/164; 604/174; 606/185; 606/191
[58] Field of Search .................. 604/164, 167, 177, 180, 604/264; 606/167, 185, 191, 192, 194

[56] References Cited

U.S. PATENT DOCUMENTS

| | | | |
|---|---|---|---|
| Re. 31,855 | 3/1985 | Osborne | 604/161 |
| 4,166,469 | 9/1979 | Littleford | 128/784 |
| 4,306,562 | 12/1981 | Osborne | |
| 4,776,846 | 10/1988 | Wells | |
| 4,813,929 | 3/1989 | Semrad | 604/51 |
| 4,969,875 | 11/1990 | Ichikawa | 604/164 |

FOREIGN PATENT DOCUMENTS

| | | |
|---|---|---|
| 2565815 | 12/1985 | France |
| 61-10698 | 4/1986 | Japan |
| 62-78938 | 5/1987 | Japan |

*Primary Examiner*—Michael H. Thaler
*Attorney, Agent, or Firm*—Armstrong, Westerman, Hattori, McLeland & Naughton

[57] ABSTRACT

A device for forming an inserting hole comprising at least two tubes having different outer diameters, and at least one of a guide wire and a sticking needle. A largest diameter tube has at its thick-walled end at least one longitudinal and approximately linear tearing line. The largest diameter tube, after being inserted into the body, can be torn using the tearing line and fixed to the skin of a patient by sewing a folded portion of the tube on the skin. The tube is not moved by the breathing or pressure since it is fixed to the skin. When the tearing line is formed by an ultrasonic cutter, width of the tearing line can be made narrow thereby preventing adhesion of bacteria to a cut portion and unexpected opening of the tearing line in the body.

12 Claims, 3 Drawing Sheets

FIG.9       PRIOR ART

DEVICE FOR FORMING AN INSERTING HOLE AND METHOD OF USING AND MAKING THE SAME

This application is a continuation of application Ser. No. 07/895,419, filed Jun. 5, 1992, now abandoned, which is a continuation of application Ser. No. 07/630,582, filed Dec. 20, 1990, abandoned.

BACKGROUND OF THE INVENTION

The present invention relates to a device for forming an inserting hole, and more particularly to a device used for forming an inserting hole for an endoscope, a drainage tube and the like. The inserting hole for an endoscope serves to allow insertion of the endoscope into diseased portions of the body in the treatment of cholangia diseases, nephrosis and the like, while the inserting hole for a drainage tube serves to allow insertion of the drainage tube into diseased portions of the body and removal treatment of bile, calculus and the like in the treatment of cholangia diseases, nephrosis and the like. Though the device of the present invention can be used for forming an inserting hole for an endoscope, a drainage tube and the like as stated above, the following explanation is mainly based on a device for forming an inserting hole for an endoscope.

Hitherto, percutaneous treatments using endoscopes have been carried out for various sickness in the bile duct, cholecyst, renal pelvis or ureter. That is, fibrous cells are formed around a tube as a reaction of the organism to foreign material by percutaneously inserting the tube having a diameter of 5 to 6 mm necessary for the insertion of the endoscope into duct organs such as bile duct, cholecyst, renal pelvis and the like. A fistula is thus formed and the endoscope is put in or out through the fistula to carry out the treatment.

In the conventional endoscope treatment, a small diameter tube is gradually exchanged at an interval of few days to one week for such tube as having a larger outer diameter in about an month, thereby forming a large diameter fistula allowing the insertion of endoscopes. Thus, the conventional method has problems that it takes a lot of time to form a fistula and gives a great pain to a patient.

As a method for shortening a period required for the above-mentioned operation or treatment, there is proposed, in Japanese Unexamined Utility Model Publication No. 78938/1987, a set for expanding a fistula for bile drainage comprising a small diameter tube allowing a metallic guide wire to pass through a center thereof, a medium diameter tube covering an outer periphery of the small diameter tube, and a large diameter tube covering the outer periphery of the small diameter tube and having an outer diameter larger than that of the medium diameter tube.

In various treatments using an endoscope such as lithotripsy, polypectomy and the recovery of the removed tissue, however, it is necessary to completely pull out the endoscope many times while holding the tissue or calculus. Therefore a fistula between the chest wall and the surface of the liver or between the retro abdominal wall and kidney is required to adhere securely. A large diameter tube having a diameter of 5 to 6 mm is required to be kept in the fistula for a few weeks to complete the formation of a strong fistula. Such method gives a great pain to a patient.

Further, there is proposed another device in which an endoscope is inserted into a hollow portion of a large diameter tube while leaving the large diameter tube in the body. In such a device, however, a diaphragm positioned on the boundary between lungs and a liver moves up and down each time a patient breathes, and the liver moves up and down with the movement of the diaphragm. As a result, there is caused a problem that the position of the large diameter tube moves. There is also a problem that a part of the large diameter tube positioned on the boundary between a chest wall and a surface of the liver bends each time a patient breathes, and the large diameter tube is broken.

In order to solve the above-mentioned drawbacks, the present inventors have variously investigated and found out that the above-mentioned drawbacks are solved by applying a tube having a longitudinal tearing line described in, for example, Japanese Examined Utility Model Publication No. 10698/1986 to a largest diameter tube, by tearing a part of the tearing line to fold one end of the tube, and by sewing the folded portion of the tube on a skin of the patient to fix the largest diameter tube.

The above tearing lines of tubes are conventionally formed by means of a knife cutter or a heat cutter. In the case of the tearing line formed by means of a heat cutter, however, both edges of a cut portion 14 are bulged due to heat of a heat cutter as shown in FIG. 9 illustrating a section of a thick-walled portion of a tube, so that a surface of the thick-walled portion shrinks and deforms at the bulged portion. Accordingly, a tissue of the body is sometimes injured when the tube is inserted into or pulled out from the body. Further, a tube is not necessarily opened along a tearing line when the end of the tube is outwardly opened with hands. Still further, in the case of a knife cutter, if the knife cutter is not sufficiently sterilized, there is a danger that bacteria adhere to a cut portion when cutting a tube so that subcutaneous tissue or duct organs such as bile duct of a patient are contaminated.

In particular, it is difficult in the case of these cutters to adjust length and width of the cut portion of the tube to desired values, so that tubes having predetermined quality are hard to obtain. Therefore, a tube is pressed by a pressure of subcutaneous tissue so that a tearing line thereof is sometimes broken to damage cell tissue. Moreover, the tearing line of the tube formed by these cutters has a large cutting width. Accordingly, a patient is sometimes infected with bacteria adhered to a cut portion of the tube, and tissue of the body is injured when inserting or pulling out a tube.

It is an object of the present invention to provide a device for forming an inserting hole capable of reducing damage of tissue of the body as much as possible and carrying out operations or treatments using endoscope or drainage tube in a short time.

SUMMARY OF THE INVENTION

In accordance with the present invention, there is provided a device for forming an inserting hole comprising at least two tubes made of synthetic resin having different outer diameters, a small diameter tube being designed to be inserted into a hollow portion of a larger diameter tube; and at least one of a guide wire and a sticking needle; wherein a largest diameter tube is made flexible, an outer diameter of the largest diameter tube is reduced to be taper-shaped at a tip portion thereof, and the largest diameter tube has at its thick-walled end at least two; and longitudinal and approximately linear tearing lines.

The present invention further provides a device for forming an inserting hole wherein the tearing line of the largest diameter tube is formed by an ultrasonic cutter.

The present invention still further provides a device for forming an inserting hole wherein a width of a cut portion in the largest diameter tube is from 0.01 to 1 mm and a depth of the cut portion is from 20 to 80% to the thickness of the tube.

In the device of the present invention, a sticking needle which is inserted into a smallest diameter tube is sticked into duct organs such as bile duct, cholecyst, renal pelvis or ureter, and then is pulled out while leaving the tube as it is in the duct organs. After a medium diameter tube is put on the smallest diameter rube to expand a fistula, the smallest diameter tube is pulled out. Thus, the fistula is gradually expanded by increasing the diameter of the tube to be put on. The fistula is finally formed by a largest diameter tube having a tearing line. The tearing line which remains outside the body is torn and the torn portion of the tube is folded and sewed on the skin of the patient. Thereafter, an endoscope is inserted into a hollow portion of the tube and is introduced to duct organs. A tip of the tube remaining in the body is positioned in the duct organs, thereby preventing damages of body tissue caused by frequent insertion and pulling out of the endoscope. After observation using the endoscope, a drainage tube is inserted into the tube remaining in the body to remove bile or calculus.

BRIEF EXPLANATION OF THE DRAWINGS

FIG. 9 is a sectional view of the largest diameter tube in which a tearing line is formed by a heat cutter.

DETAILED DESCRIPTION

Next a device of the present invention is explained based on the accompanying drawings.

Figure 1:
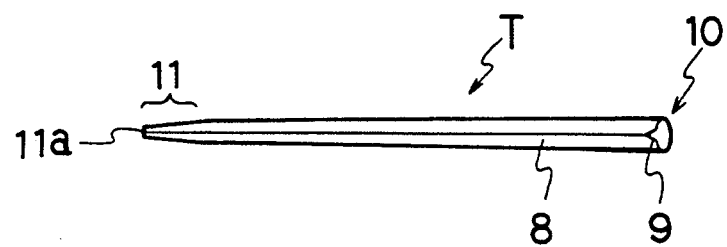
FIG. 1 is a perspective view of an example of a largest diameter tube in a device of the present invention.
Figure 8:
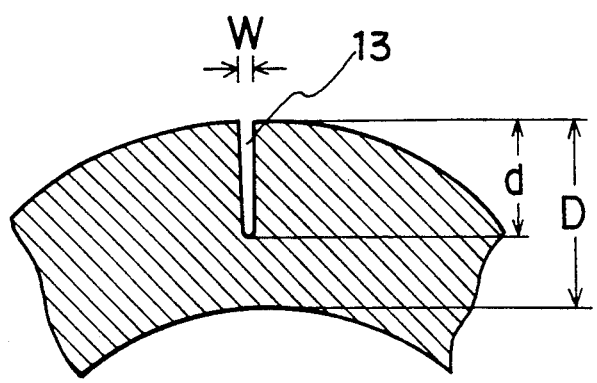
FIG. 8 is a sectional view of the largest diameter tube in the device of the present invention.
Figure 8:
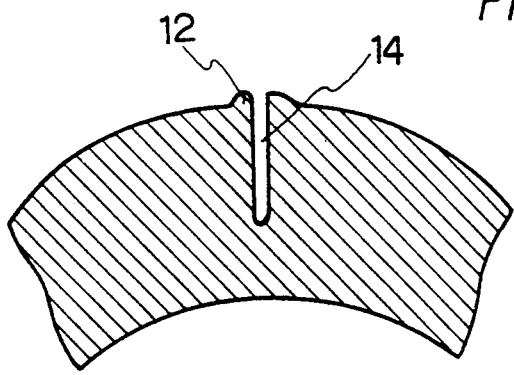

FIG. 1 is a perspective view of an example of a largest diameter tube in a device cf the present invention. The tube T comprises a tubular body made of flexible synthetic resin, and has, on the outer surface thereof, at least one approximately linear tearing line or groove (hereafter referred to as tearing line) in the longitudinal direction of the tube T. The tearing line 8 extends from a notch 9 at a base portion 10 of the tube T to a tip 11a thereof. The tearing line 8 is formed by an ultrasonic cutter. A cut portion 13 which provides the tearing line 8 does not form bulged portions on both sides of the cut portion 13 as shown in FIG. 8 illustrating a sectional view of the thick-walled portion of the tube. The cut portion 13 is half-cut by the ultrasonic cutter, and the width W thereof is approximately equal over the whole depth d thereof. The depth d is preferably from 20 to 80%, more preferably from 35 to 75% to the thickness D of the thick-walled portion of the tube. When the ratio is less than 20%, the tearing of the tube becomes difficult so that there is a tendency that the tube is not torn along a tearing line. On the other hand, when the ratio is more than 80%, the breaking strength of the tube tends to be lowered, and there is a danger that the tube is broken along the tearing line by the pressure of subcutaneous tissue before the endoscope is inserted into the tube so that body fluid enters the inside of the tube. In FIG. 1, the tearing line 8 extends from the base portion 10 of the tube to the tip 11a thereof. However, a tearing line might be formed only on such portion of the tube that is outside the body and might not be formed on such portion of the tube that is inside the body. The depth d of the cut portion can be controlled by moving an ultrasonic cutter as it swings without changing a distance between an edge of the cutter and a surface of the roll, or moving the ultrasonic cutter horizontally while keeping a distance between the edge of the cutter and a tube-receiving table constant. In cutting a tube, a laser measuring instrument capable of measuring up to 1 mm is used to adjust dimensions, thereby the depth d of the tube can be determined at will. Only a cut portion of the tube is locally melted and solidified by frictional heat generated by minute vibration of the edge of the ultrasonic cutter. The width W of the cut portion 13 can be determined at will depending on objects of tubes, and is not particularly limited in the present invention. However, the value thereof is usually from 0.01 to 1.0 mm, preferably from 0.01 to 0.6 mm. When the width W is less than 0.01 mm, tearing of the tube tends to become difficult. On the other hand, when the width W is more than 1.0 mm, there is a danger that external bacteria adhere to the cur portion and the tearing line 8 tends to open in the body tissue. If the width W of the cut portion 13 is not more than 0.2 mm, existence of the tearing line is almost inconspicuous so that the tearing line does not spoil the beauty of the tube.

As materials of tubes, fluororesin, polyurethane, silicone resin, polyvinylchloride, polypropylene, polyethylene, ethylene-propylene copolymer, poly(ethylene butylene)polystyrene block copolymer, polyamide, polyethylene terephthalate or copolymer thereof, and mixtures thereof can be used. Among them, it is preferable to use polyolefine such as polypropylene and polyethlene since they are not easily cut by high-frequency wave cutter. As materials for tubes for forming a fistula (i.e. tubes other than the largest diameter tube having a tearing line), synthetic resin slightly harder than material for the largest diameter tube can be preferably used.

In the tube shown in FIG. 1, a tearing line 8 extends approximately linearly from a base portion 10 of the tube to a tip 11a thereof. When the tube is torn to the midway thereof and is folded, a tearing line might not be necessarily formed from the base portion to the tip of the tube. A notch 9 is formed at a base portion 10 of the tube to facilitate the tearing of the tube. A breaking plug (not shown) might be formed at the base portion for the same reason.

At least two tearing lines 8 are formed on the surface of the tube in the longitudinal direction thereof. When forming not less than two tearing lines, folding of the tube becomes easy. In particularly, it is preferable to form two tearing lines at opposite positions to each other. The tip portion 11 of the tube T is tapered toward the tip 11a thereof in order that an inner surface of the tip portion 11 of the tube closely contact with an outer surface of the endoscope or drainage tube and that body fluid and the like does not enter the clearance between the tube and the endoscope or drainage tube.

Next, there is explained an example of method of using a device of the present invention based on FIGS. 2 to 7. In FIGS. 2 to 7, A, B and C are liver, bile duct and gall bladder, respectively.

Figure 2:
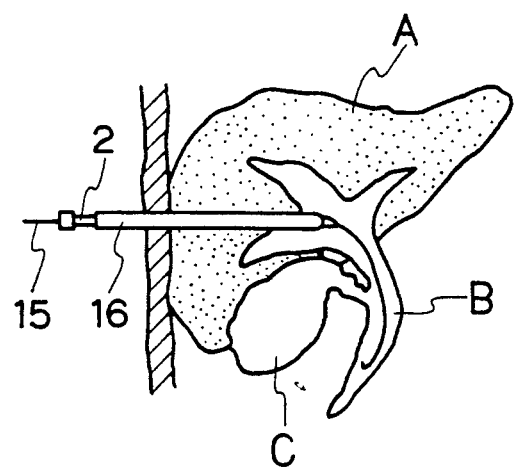
FIGS. 2 to 7 are explanatory views showing a method of using the device of the present invention.

A sticking needle 2 is inserted into a small diameter tube 16 and a tip of the sticking needle 2 projects from a tip portion of the tube 16. It is preferable that the tip portion of the tube 16 is tapered toward the tip thereof in order that an inner surface of the tip portion of the tube closely contact with an outer surface of the sticking needle 2. The sticking needle 2 inserted into the tube 16 is inserted into the body of a patient as shown in FIG. 2, and a tip of the sticking needle 2 is introduced to a bile duct B through subcutaneous tissue. In that case, introduction of the tube 16 into the bile duct B can be carried out smoothly if a flexible guide wire 15 is inserted into a hollow portion of the sticking needle 2, the sticking needle 2 is pulled out, and thereafter the guide wire is inserted into the tube.

Figure 3:
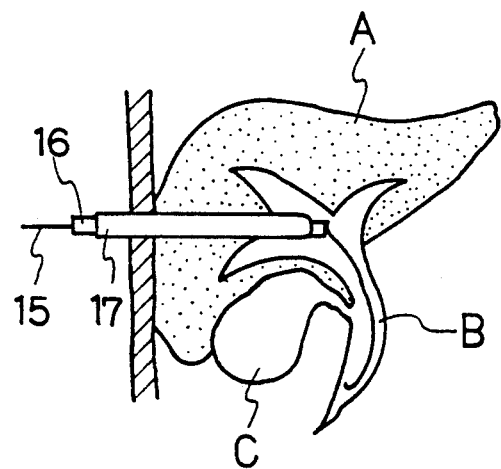

A medium diameter tube 17 having a diameter larger than that of the small diameter tube 16 is put on the tube 16 as shown in FIG. 3 to expand the fistula. After pulling out the small diameter tube 16, a large diameter tube 18 is put on the medium diameter tube to further expand the fistula.

Figure 4:
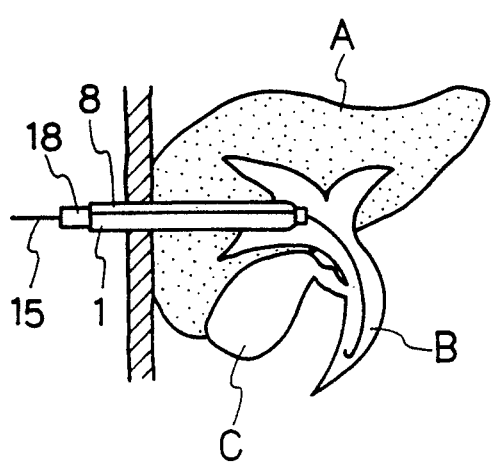
Figure 5:
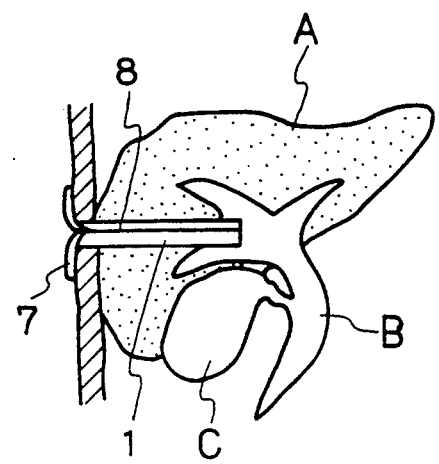

Finally, a largest diameter tube 1 is put on the large diameter tube 18 as shown in FIG. 4 to still further expand the fistula. Then, a tearing line outside the body is folded, and the tube 1 is fixed to the skin of the patient to sewing the folded portion of the tube on the skin. Though the folded portion of the tube is sewed on the skin in FIG. 5, the tube can be fixed to the skin by means of a suitable fixing device.

Figure 6:
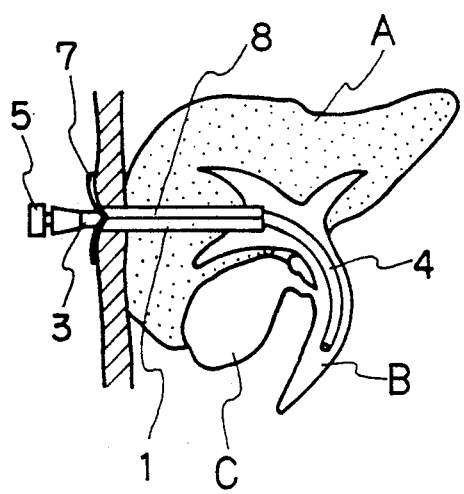

Thereafter, an endoscope 3 is inserted into a hollow portion of the tube 1 as shown in FIG. 6 until a tip portion of the endoscope appears in the bile duct B. The endoscope 3 has such structure that an eyepiece portion 5, a flexible tube 4, a bending tube and a tip portion are connected to each other in this order. Image guide fibers, light guide fibers and the like are provided inside the endoscope 3. The endoscope 3 has a bending operation device for carrying out operation of the bending tube besides an eyepiece portion 5 for observation. After examining various choloangia diseases such as choledocholithiasis, choledochiarctia, cholecystolithiasis and cholecystic polyp, ureterostenosis, ureterolithiasis and nephrosis with the use of the endoscope, the endoscope 3 is removed while leaving the tube 1 in the body.

Figure 7:
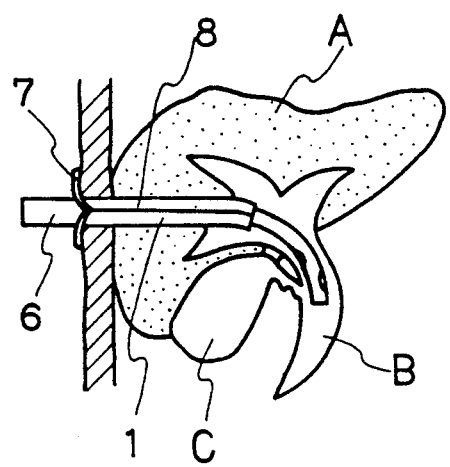

Next, a drainage tube 6 is inserted into the tube 1 left in the body until a tip of the drainage tube 6 reaches a diseased portion as shown in FIG. 7. The drainage tube 6 is used, for example, to suck out bile for relieving jaundice. A drainage tube having a tapered tip and a circular end opening can be used as well as a drainage tube having a closed end and a plurality of small holes on the side portion thereof. Besides a drainage tube, a catheter can be inserted into the tube left in the body until the tip of the catheter reaches the diseased portion to inject liquid drug.

An example of each element of the device is now explained in detail hereinafter.

A guide wire 15 serves to guide a small diameter tube 16 put on the guide wire 15 to a portion to which an endoscope is applied. The guide wire 15 is made of metal such as stainless steel. The shape of a tip portion of the guide wire varies depending on portions to which the guide wire is applied. For example, in the case of application for bile duct, there has been used a guide wire call "J guide wire" of which tip portion has a characteristic of elastically bending in a J-shaped manner. The J guide wire is inserted into the tube with keeping the tip portion thereof straight, and the tip portion curves in a J-shaped manner when it projects from an opening of the tip portion of the tube, so that the bile duct is not damaged.

As a small diameter tube 16, such a tube as having an inner diameter of about 1 mm, an outer diameter of 3.4 mm and a total length of 50 cm is used to fit sizes of the guide wire 15. The small diameter tube 16 has a high resiliency and is made of slightly hard synthetic resin. The outer diameter of a tip portion of the small diameter tube is gradually reduced toward its end to be taper-shaped.

A medium diameter tube 17 has an inner diameter of 3.4 mm so as to cover the outer periphery of the small diameter tube 16, and has an outer diameter of 4.7 mm and a total length of about 20 cm. The medium diameter tube is made of slightly hard synthetic resin and has a tip portion of which outer diameter is gradually reduced toward its end to be taper-shaped like the small diameter tube 16.

A medium large diameter tube has an inner diameter of 3.4 mm so as to cover the outer periphery of the small diameter tube 16, and has an outer diameter of 5.3 mm which is larger than that of the above-mentioned medium diameter tube 17. A total length of the medium large diameter tube is about 20 cm like the medium diameter tube 17. Material and shape of a tip portion of the medium large diameter tube 18 are the same as the medium diameter tube 17.

A large diameter tube has an inner diameter of 3.4 mm so as to cover the outer periphery of the small diameter tube 16, and has an outer diameter of 6.0 mm which is larger than that of the above-mentioned medium large diameter tube. A total length of the large diameter tube is about 20 cm like the medium diameter tube 17. Material and shape of a tip portion of the large diameter tube 18 are the same as the medium diameter tube 17.

A largest diameter tube 1 enables the insertion and pulling out of an endoscope, and the insertion of a drainage tube 6. The tube 1 has an inner diameter of 6.0 mm, an outer diameter of 6.3 mm, and a total length of about 20 cm. Unlike the above-mentioned tubes 16, 17 and 18, it is preferable to make the tube 1 thin as long as it maintains rigidity.

The drainage tube 6 serves to remove waste in the duct organs after the examination using an endoscope is over. The tube 6 is inserted into a hollow portion of the largest diameter tube 1, and has an inner diameter of 3.4 mm, an outer diameter of 6.0 mm and a total length of about 33 cm. The drainage tube is made of soft synthetic resin and has a high flexibility and resiliency. A plurality of side holes for discharging fluid are provided at a tip portion of the drainage tube 6.

EXAMPLES 1 TO 12

Polytetrafluoroethylene (Examples 1 to 6) or tetrafluoroethylene perfluoroalkylvinylether copolymer (Tefron 350-J produced by Du Pont-Mitsui Fluorochemicals Company, Ltd.,) (examples 7 to 12) was melted and extruded to form a tubular body having an inner diameter of 6.1 mm, an outer diameter of 6.6 mm, a thickness of a thick-walled portion of 0.25 mm, and a length of 90 mm. At one end of the tubular body, two notches 9 shown in FIG. 1 were formed at opposite positions. Then, two approximately linear tearing lines 8 were formed from notches 9 to the other end of the tubular body 8 by the use of an ultrasonic cutter (T-02 produced by Nippon Thermonics Co., Ltd.,). Width of the tearing line 8 was fixed to 0.06 mm, while depth of a cut portion was varied as shown in Table 1. Tearing strength when the tube was torn from notches 9 of the tube are summarized in Table 1. The tearing strength was measured by the use of an auto-graph instrument (S-500D produced by Shimadzu Corporation) under the conditions of a distance between chucks of 50 mm and a cross head speed of 200 mm per minute. Tubes were opened in a direction at 180 degrees to each other.

Generations of tearing in the tearing lines when tubes were pressed in the direction of connecting two tearing lines were tested. The number of test samples was 100, and proportion defective was measured. Further, tubes were opened to form sheets having a width of 12.7 mm, and bending life was measured by MIT Folding Endurance method prescribed in ASTM-D-2157. These results are summarized in Table 1.

TABLE 1

| No. | Depth of cutting portion d ($\mu$m) | d/D (%) | Tearing strength (kg) | Proportion defective (%) | Bending life (times) |
|---|---|---|---|---|---|
| Ex. 1 | 210 | 84 | 0.26 | 5 | $33.7 \times 10^4$ |
| Ex. 2 | 180 | 72 | 0.51 | 1 | $35.7 \times 10^4$ |
| Ex. 3 | 150 | 60 | 0.69 | 0 | $36.4 \times 10^4$ |
| Ex. 4 | 120 | 48 | 0.80 | 0 | $37.8 \times 10^4$ |
| Ex. 5 | 70 | 28 | 1.00 | 0 | $39.1 \times 10^4$ |
| Ex. 6 | 40 | 16 | 1.23 | 0 | $40.3 \times 10^4$ |
| Ex. 7 | 210 | 84 | 0.34 | 2 | $29.7 \times 10^4$ |
| Ex. 8 | 180 | 72 | 0.48 | 0 | $32.5 \times 10^4$ |
| Ex. 9 | 150 | 60 | 0.61 | 0 | $37.1 \times 10^4$ |
| Ex. 10 | 120 | 48 | 0.83 | 0 | $39.3 \times 10^4$ |
| Ex. 11 | 70 | 28 | 0.97 | 0 | $40.4 \times 10^4$ |
| Ex. 12 | 40 | 16 | 1.18 | 0 | $42.0 \times 10^4$ |

As is clear from Table 1, with the increase of ratio of the depth d to the sheet thickness D, tearing strength when the tube is opened from notches decreases, generation ratio of tearing in the tearing lines when tubes are pressed increases, and bending life is shortened.

According to a device of the present invention, damage of organs of the body is reduced, and endoscopes, drainage tubes and the like can be introduced into diseased portions in a short time. A largest diameter tube in the present invention has a function as a fistula, so that the period of forming the fistula is not at all required, pains of the patient can be greatly decreased, and the endoscope and the like can be inserted into and pull out from the human body smoothly.

Further, the largest diameter tube can be fixed to the body safely and in a short time with reducing damage of organs of the body. The tube does not move by the breathing of a patient and pressure, since the tube is sewed and fixed to the skin of the patient.

Width of the tearing line of the tube is small, so that external bacteria do not adhere to a cut portion of the tearing line and not infect the inside of the body. Further, the tearing line of the tube is not teared by a pressure of subcutaneous tissue and does not cause damage of cell organs when a tip of the endoscope and the like is guided into duct organs such as bile duct and the endoscope is pulled out from the body.

By using an ultrasonic cutter, a tearing line having a narrow width and a desired depth can be obtained. In that case, bulged portions which appear in the case of a heat cutter are not formed on both ends of a cut portion, so that the tube can be opened smoothly along the tearing line when opening outwardly from the tearing line. Thus, the tube can be torn at a desired time and to a necessary portion, so that damage of organs of the body caused by frequent insertion and pulling out of endoscopes, drainage tubes, catheters and the like can be prevented. Further, since the bleeding can be prevented, treatments in the operation can be carried out easily and the recovery after treatments can be advanced.

What is claimed is:

1. A device for forming an inserting hole comprising:
   at least two tubes made of synthetic resin having different outer diameters, a smaller diameter tube being designed to be inserted into a hollow portion of a larger diameter tube;
   at least one of a guide wire and a sticking needle for insertion within one of said at least two tubes;
   wherein a tube having a largest diameter has at least two longitudinal linear tearing lines formed in an outer surface thereof and extending from a base portion thereof toward a tip portion thereof;
   wherein the width of each of the linear tearing lines is between 0.01 mm and 1 mm, and a ratio of a depth to the thickness of the tube having the largest diameter for each of the tearing lines is between 20% and 80%;
   wherein the width of the tearing lines is approximately equal over a substantial portion of the depth; and
   wherein said outer surface has a substantially constant curvature free from bulges on opposite sides of each of said linear tearing lines.

2. The device of claim 1, wherein the tearing lines of the largest diameter tube is formed by an ultrasonic cutter.

3. The device of claim 1, wherein the width of each of the tearing lines is between 0.01 mm and 0.6 mm, and a ratio of a depth to the thickness of the tube having the largest diameter for each of the tearing lines is between 35% and 75%.

4. The device of claim 1, wherein the largest diameter tube comprises a polyolefine material.

5. The device of claim 1, wherein the largest diameter tube comprises a material from the group consisting of polypropylene and polyethylene.

6. The device of claim 1, wherein each said tearing lines extends along substantially only a portion of the tube that is constructed to extend outside of the body of a patient.

7. The device of claim 1, wherein each said tearing lines extends to substantially near said tip portion.

8. A device for forming an inserting hole in a patient, comprising:
   at least two tubes made of synthetic resin having different outer diameters, a smaller diameter tube being designed to be inserted into a hollow portion of a larger diameter tube;
   at least one of a guide wire and a sticking needle for insertion within one of said at least two tubes;
   wherein a tube having a largest diameter has a means for enabling folding of a portion of the tube having a largest diameter against the external side of the patient;
   wherein said means for enabling folding includes at least two longitudinal linear tearing lines formed in an outer surface of said tube having a largest diameter and extending from a base portion thereof toward a tip portion thereof;
   wherein the width of each of the linear tearing lines is between 0.01 mm and 1 mm, and a ratio of a depth to the thickness of the tube having the largest diameter for each of the tearing lines is between 20% and 80%;

wherein the width of the tearing lines is approximately equal over a substantial portion of the depth;

wherein said outer surface has a substantially constant curvature free from bulges on opposite sides of each of said linear tearing lines; and including means for attaching folded portions of said tube having largest diameter, which have been folded by tearing said tube having largest diameter along said tearing lines, to the external side of a patient.

9. The device of claim 8, wherein said means for attaching includes threads for sewing to the skin of a patient.

10. A method of making a device for forming an inserting hole, comprising the steps of:

providing at least two tubes made of synthetic resin having different outer diameters, a smaller diameter tube being designed to be inserted into a hollow portion of a larger diameter tube;

providing at least one of a guide wire and a sticking needle for insertion within one of said at least two tubes;

ultrasonically cutting a tube having a largest diameter to form at least two longitudinal linear tearing lines formed in an outer surface thereof and extending from a base portion thereof toward a tip portion thereof;

wherein the width of each of the linear tearing lines is formed between 0.01 mm and 1 mm, and a ratio of a depth to the thickness of the tube having the largest diameter for each of the tearing lines is formed between 20% and 80%, wherein the width of the tearing lines is formed approximately equal over a substantial portion of the depth, and wherein said outer surface is formed with a substantially constant curvature free from bulges on opposite sides of each of said linear tearing lines.

11. A method of forming an inserting hole, comprising the steps of:

(1) providing a device for forming an inserting hole comprising at least two tubes made of synthetic resin having different outer diameters, a smaller diameter tube being designed to be inserted into a hollow portion of a larger diameter tube, at least one of a guide wire and a sticking needle for insertion within one of said at least two tubes, wherein a tube having a largest diameter has at least two longitudinal linear tearing lines formed in an outer surface thereof and extending from a base portion thereof toward a tip portion thereof, wherein the width of each of the linear tearing lines is between 0.01 mm and 1 mm, and a ratio of a depth to the thickness of the tube having the largest diameter for each of the tearing lines is between 20% and 80A%, wherein the width of the tearing lines is approximately equal over a substantial portion of the depth, and wherein said outer surface has a substantially constant curvature free from bulges on opposite sides of each of said linear tearing lines;

(2) inserting said device into the body of an individual;

(3) tearing a portion of the largest diameter tube extending out of the individual along the tearing lines so as to create folded portions; and (4) attaching the folded portions of said tube having the largest diameter to the outside surface of the skin of the individual.

12. The method of claim 11, wherein said step (4) of attaching the folded portions includes sewing the folded portions to the skin of the individual.

* * * * *